(12) United States Patent
Ronda et al.

(10) Patent No.: US 9,931,426 B2
(45) Date of Patent: Apr. 3, 2018

(54) AIR PURIFICATION DEVICE, A LIGHTING DEVICE AND A LUMINAIRE

(71) Applicant: PHILIPS LIGHTING HOLDING B.V., Eindhoven (NL)

(72) Inventors: Cornelis Reinder Ronda, Eindhoven (NL); Lucas Johannes Anna Maria Beckers, Eindhoven (NL); Susanne Maaike Valster, Eindhoven (NL)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days.

(21) Appl. No.: 15/502,183

(22) PCT Filed: Jun. 26, 2015

(86) PCT No.: PCT/EP2015/064490
§ 371 (c)(1),
(2) Date: Feb. 6, 2017

(87) PCT Pub. No.: WO2016/020115
PCT Pub. Date: Feb. 11, 2016

(65) Prior Publication Data
US 2017/0224865 A1 Aug. 10, 2017

(30) Foreign Application Priority Data
Aug. 7, 2014 (EP) .................................. 14180203

(51) Int. Cl.
*A61L 9/20* (2006.01)
(52) U.S. Cl.
CPC ........... *A61L 9/205* (2013.01); *A61L 2209/12* (2013.01)
(58) Field of Classification Search
CPC ................... A61L 2209/12; A61L 9/16–9/205
See application file for complete search history.

(56) References Cited

U.S. PATENT DOCUMENTS

| 5,919,422 A | 7/1999 | Yamanaka et al. |
| 2008/0305004 A1 | 12/2008 | Anderson et al. |

(Continued)

FOREIGN PATENT DOCUMENTS

| CN | 103712122 A | 4/2014 |
| EP | 2527769A2 A2 | 11/2012 |

(Continued)

OTHER PUBLICATIONS

"Inactivation of Bacterial Pathogens Following Exposure to Light From a 405-Nanometer Light-Emitting Diode Array", by M. Maclean, et al., Appl. Environ. Microbiol. 75(7):1932-1937, Jul. 15, 2010.

(Continued)

*Primary Examiner* — Timothy C Cleveland

(57) ABSTRACT

An air purification device (100), a lighting device and a luminaire are provided. The air purification device comprises an air inlet (132), an air outlet (134), a photocatalytic volume (150), a first solid state light emitter (102) and a second solid state light emitter (122). The air inlet receives an air flow (140). The photocatalytic volume comprises a photocatalytic material and the air flow flows through the photocatalytic volume to contact some air with the photocatalytic material. The photocatalytic volume is between the air inlet and the air outlet. The photocatalytic material is a catalyst under the influence of UV light in photoreactions between gasses in the air flow. The first solid state light emitter emits UV light towards the photocatalytic volume. The second solid state light emitter emits deep blue light towards the photocatalytic volume. The deep blue light has a peak wavelength in between (400) nanometer and (450) nanometer.

12 Claims, 5 Drawing Sheets

(56) References Cited

U.S. PATENT DOCUMENTS

| | | | |
|---|---|---|---|
| 2009/0041632 A1* | 2/2009 | Day | A61L 9/205 422/121 |
| 2010/0246169 A1 | 9/2010 | Anderson et al. | |
| 2013/0094204 A1 | 4/2013 | Budai et al. | |

FOREIGN PATENT DOCUMENTS

| | | |
|---|---|---|
| JP | 11300161 A | 11/1999 |
| JP | 2004031250 A | 1/2004 |
| JP | 2004166996 A | 6/2004 |
| JP | 2005101458 A | 4/2005 |
| JP | 2009090260 A | 4/2009 |
| KR | 20110077804 A | 7/2011 |
| WO | WO2014097089A1 A1 | 6/2014 |

OTHER PUBLICATIONS

Nature Chemistry, vol. 3, Issue 4, pp. 296-300 (2011).

* cited by examiner

AIR PURIFICATION DEVICE, A LIGHTING DEVICE AND A LUMINAIRE

CROSS-REFERENCE TO PRIOR APPLICATIONS

This application is the U.S. National Phase application under 35 U.S.C. § 371 of International Application No. PCT/EP2015/064490, filed on Jun. 26, 2015, which Claims the Benefit of European Patent Application No. 14180203.3, filed on Aug. 7, 2014. These applications are hereby incorporated by reference herein.

FIELD OF THE INVENTION

The invention relates to air purification device. The invention further relates to lighting devices comprising an air purification device and to luminaires comprising a lighting device.

BACKGROUND OF THE INVENTION

Published patent application WO2014/097089, which is incorporated by reference, discloses a lighting unit and a luminaire for illumination and for purifying air. The lighting unit comprises a photocatalytic volume through which, in use, air flows. The photocatalytic volume comprises photocatalytic material that is configured to be a catalyst in photoreactions between gasses in the air flow under the influence of light that impinges on the material. The lighting unit at least comprises a solid state light emitter that emits light towards the photocatalytic volume and the emitted light at least comprises light that assists the photoreactions between the gasses in the air flow.

The photocatalytic volume of the lighting unit of the cited document comprises open spaces, such as pores or holes, through which the air flow is able to flow from one side of the photocatalytic volume to another side of the photocatalytic volume. In many typical use cases it might be that inside these open spaces, or at the entry windows of the open spaces, bacteria colonies start to grow because such bacteria are delivered from the ambient onto the surfaces of the photocatalytic volume by the air flow and because there is quite often a relatively good climate for such bacteria to grow in the lighting unit. In relatively humid and/or warm climates, water may condensate in the lighting unit and then the water and the relatively high temperature provide a very good climate for the bacteria to grow. If too many colonies of bacteria are formed, no effective air purification is possible anymore because the photocatalytic volume may become less permeable for air and the bacteria or debris of the bacteria may provide unpleasant compounds (in the gaseous phase) to the air that flows through the photocatalytic volume. Furthermore, the large number of bacteria colonies may induce health risks because the gasses released by the bacteria or the debris may be poisonous and/or more bacteria may be present in the air flow that leaves the lighting unit of the cited patent application than there are present in the flow that enters the lighting unit.

SUMMARY OF THE INVENTION

It is an object of the invention to provide an air purification device that is safer than known air purification devices. A first aspect of the invention provides an air purification device. A second aspect of the invention provides a lighting device. A third aspect of the invention provides a luminaire. Advantageous embodiments are defined in the dependent claims.

An air purification device for purifying air in accordance with an aspect of the invention comprises an air inlet, an air outlet, a photocatalytic volume, a first solid state light emitter and a second solid state light emitter. The air inlet is for receiving an air flow. The photocatalytic volume comprises a photocatalytic material and is configured to allow air to flow through the photocatalytic volume such that at least a portion of the air flowing through the photocatalytic volume contacts the photocatalytic material. The photocatalytic volume is arranged between the air inlet and the air outlet to ensure that, in use, at least a portion of the air flow received by the air inlet flows through the photocatalytic volume. The photocatalytic material being configured to be a catalyst under the influence of UV light in photoreactions between gasses in the air flowing through the photocatalytic volume. The first solid state light emitter is configured to emit UV light and is arranged to emit the UV light towards the photocatalytic volume for activating the photocatalytic material to act as the catalyst in the photoreactions between the gasses in the air flowing through the photocatalytic volume. The second solid state light emitter is configured to emit deep blue light in a light emission spectrum having a peak wavelength in the range from 400 nanometer to 450 nanometer. The second solid state light emitter is arranged to emit the deep blue light towards the photocatalytic volume.

The air purification device operates, in use, as an air purifier because air flows along photocatalytic material that is activated by the UV light that impinges on the photocatalytic material and, thus, hazardous or unpleasant gasses in the air flow may react towards less hazardous or unpleasant gasses. The photocatalytic volume also receives the deep blue light. The deep blue light acts as light that disinfects the photocatalytic volume. Bacteria are killed by this light. As such, most of the bacteria will not settle in the photocatalytic volume and cannot grow into large colonies. Thereby it is prevented that the photocatalytic volume become less effective because air passages of the photocatalytic volume (through which, in use, the air flows through the photocatalytic volume) are blocked or sealed by colonies of bacteria. Moreover, the risk of discharging hazardous gasses (generated by the bacteria or originating from the debris of the bacteria) via the air outlet of the air purification device is reduced. Thereby a safer air purification device is obtained.

The skilled person, who works in the field of air purifiers that use photocatalytic volumes through which the air has to flow (in use), is not aware of advantageous effects of the deep blue light. It is not obvious for him to include an additional solid state light emitter because it seems to affect the power efficiency of an air purification device too much. In his field he is only aware of preventing the bacteria by heating the air to a relatively high temperature thereby thermally killing the bacteria or he is aware of a solution in which the photocatalytic volume must be replaced or cleaned on a regular basis.

The light emission spectrum of the deep blue light has a peak wavelength within the range from 400 to 450 nm. Optionally, the peak wavelength is within a range from 405 to 445 nm. Optionally, a width of the light emission spectrum of the deep blue light is smaller than 75 nm when the width is measured as a full width half maximum value. Optionally, the width of the light emission spectrum of the deep blue light is smaller than 50 nm when the width is measured as a full width half maximum value.

The deep blue light and the UV light are emitted towards the photocatalytic volume. Thus, the light falls at least on surfaces of the photocatalytic volume that are visible from the outside. The photocatalytic volume is arranged to allow the air flow to flow through the photocatalytic volume, which means that there are at least holes or air passages. The deep blue light and the UV light may also be transmitted into the interior of the photocatalytic volume via such holes or air passages.

The air purification device further comprises a controller for controlling an on and off state of the second solid state light emitter. The controller may also be configured to control other components of the air purification device, such as, for example, the first stolid state light emitter. This enables controlling the first solid state light emitter such that the photocatalytic volume is well disinfected, while it is prevented that too much power is used. For example, the controller may be configured to control the second solid state light emitter during regular interval of time for a specific period of time in the on mode.

The controller is configured to control the second solid state light emitter also into the on state while the first solid state light emitter is not emitting light. Thus, when the air purification device is not purifying air (and is to be switched off), the photocatalytic volume is still disinfected by the deep blue light, thereby ensuring that the air purification device is relatively safe.

Often, when an air flow is introduced in devices that handles air and that are not used for a relatively large period of time, a specific smells can be sensed which is the result of, for example, metabolic products of bacteria growing in the device. This may also apply to the photocatalytic volume. This enables the disinfection of the photocatalytic volume while it seems that the air purification device is switched off. Thereby it is also prevented that after a relatively long period of time of inactivity, a bad small can be sensed when the air purification device is controlled into operation. When the first solid state light emitter is not emitting light and, thus, in the off mode, it may be that the controller controls the second solid state light emitter continuously in the on mode, or only for a limited period of time in the on mode, or during regular interval of time for a specific period of time in the on mode.

As discussed above, the disinfecting of the photocatalytic volume can be done at relatively low power levels thereby preventing that the air purification device is consuming too much power when it is not in an air purification mode. It seems logical that the second solid state light emitter is in the on mode while the first solid state light emitter is in the on state, however, the controller may also be configured to control the second light emitter for periods of time in the off mode while the first solid state light emitter is emitting light to save some energy while still maintaining an effective disinfection of the photocatalytic volume.

Optionally, 'at least the period of time' comprises one of: about the whole period of time that the first solid state light emitter is not emitting light, a limited period of time of the period of time that the first solid state light emitter is not emitting light, periods of time at regular or irregular intervals of time during the period of time that the first solid state light emitter is not emitting light.

Optionally, the light intensity of the second solid state light emitter is selected to obtain a light energy density of the deep blue light in a range from 10 to 30 mWh/cm$^2$ at the photocatalytic volume. The inventors have found that a relatively small amount of deep blue light has to impinge on the photocatalytic volume to obtain the effect of disinfecting the photocatalytic volume. Thereby, possible disadvantageous effect of additional light source, namely decreasing the power efficiency of the air purification device, are overcome while the air purification device remains safe and the air purification device remains effective.

It is to be noted that the photocatalytic volume may have well defined outer surfaces, but may have, in other embodiments, a not well defined outer surface because its structure is, for example, based on non-woven fibers. At least one is able to define an envelope around the photocatalytic volume and the envelope has certain (virtual) surfaces. The deep blue light impinges on a portion of such a (virtual) surface and, according to this embodiment, the light energy density of the deep blue light is within 10 to 30 mWh/cm$^2$ at the portion of the (virtual) planes of the envelope at which the deep blue light impinges. This light intensity if low and, thus, the first solid state light emitter may be a solid state light emitter that does not consume much power.

Optionally, the peak wavelength of the light emission spectrum of the deep blue light is in a range from 415 to 435 nanometer. It is known that deep blue light having such a peak wavelength is effective for disinfecting the photocatalytic volume.

Optionally, the UV light emitted by the first solid state light emitter has a peak wavelength in a range from 300 nanometer to 400 nanometer.

Optionally, the photocatalytic volume comprises elongated structures and the photocatalytic material is provided on at least a portion of the surfaces of the elongated structures. The elongated structures have a relatively large surface and, thus, a lot of the to-be-cleaned air can be brought in contact with the photocatalytic material provided on the relatively large surface.

Optionally, the elongated structures are fibers and, optionally, the photocatalytic volume is a woven or non-woven material made of fibers. Such embodiments of photocatalytic volumes may be compact filters that can be easily integrated into the air purification device.

Optionally, the air purification device further comprises an air flow generator for generating the air flow that is received by the air inlet. The air flow generator is, for example, a ventilator, a fan, an air blower, etc. It is to be noted that the invention is not limited to air purification devices which comprise the air flow generator because the air purification device may also be coupled to another system that generates already an air flow for receiving the air flow. Such another system is, for example, an air conditioning or air refreshment system of a building. Optionally, the above discussed controller also controls the air flow generator. For example, the controller may switch the air flow generator on and off. Or, when the air flow generator may generate an air flow of a controllable volume, the controller may control the amount of air per time unit that is moved by the air flow generator.

Optionally, the second solid state light emitter is arranged for emitting the deep blue light towards other components of the air purification device. For example, the deep blue light is also emitted towards a portion of an inner surface of a housing of the air purification device, or towards a portion of the air inlet or air outlet. Thereby more surfaces of the air purification device are disinfected. Several elements on which the deep blue light impinges may be partly reflective such that the deep blue light is reflected towards more locations to be disinfected. The second solid state light emitter may also have optical elements such as, for example a reflector for reflecting a portion of the light towards the photocatalytic volume and/or to the other components of the air purification device. Optionally, the photocatalytic volume is partially light transmitting for at least the deep blue light. This means that, for example, the air passages in the photocatalytic volume also allow a partial transmission of the deep blue light through the photocatalytic volume such that components arranged at the other side of the photocatalytic volume receive a portion of the deep blue light. The air passages in the photocatalytic volume comprises, for example, partially light reflective walls that also contribute to the transmission of light through the air passages.

According to another aspect of the invention, a lighting device is provided that comprises a light source and the air purification device according to the above discussed embodiments. The integration of a light source and the air purification device may lead to advantages with respect to obtaining a relatively compact device that may be easily installed in luminaires or light fittings in buildings. Furthermore, the power provided to the light source may be used to provide power to the air purification device.

Optionally, the lighting device comprises luminescent material. The luminescent material is configured to convert UV light towards visible light and is arranged to receive a portion of UV light emitted by the first solid state light emitter of the air purification device. The lighting device further comprises a light exit window for emitting at least a portion of the visible light towards an ambient of the lighting device. In this embodiment a portion of the UV light generated by the first solid state light emitter also impinges on the luminescent material and is converted towards visible light. Thereby the luminescent material and the first solid state light emitter of the air purification device together form the light source of the lighting device. In this embodiment no additional light sources must be provided and the light that is generated by first solid state light emitter is used more efficiently. For example, when a substantial part of the generated UV light does not contribute effectively to the air purification by the photocatalytic material, then this embodiment is in particular efficient with respect to power usage because no UV light is wasted. It may also be that the photocatalytic volume is partially build up with transparent or translucent materials to obtain a partial transmission of the deep blue light through the photocatalytic volume.

According to a further aspect of the invention a luminaire is provided that comprises a lighting device according to one of the above discussed embodiments of the lighting device.

The lighting device and the luminaire according aspects of the invention also provides the same benefits as the air purification device according to an aspect of the invention and has similar embodiments with similar effects as the corresponding embodiments of the air purification system.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

Modifications and variations of the air purification device, the lighting device and the luminaire, which correspond to the described modifications and variations of the air purification system, can be carried out by a person skilled in the art on the basis of the present description.

Figure 1A:
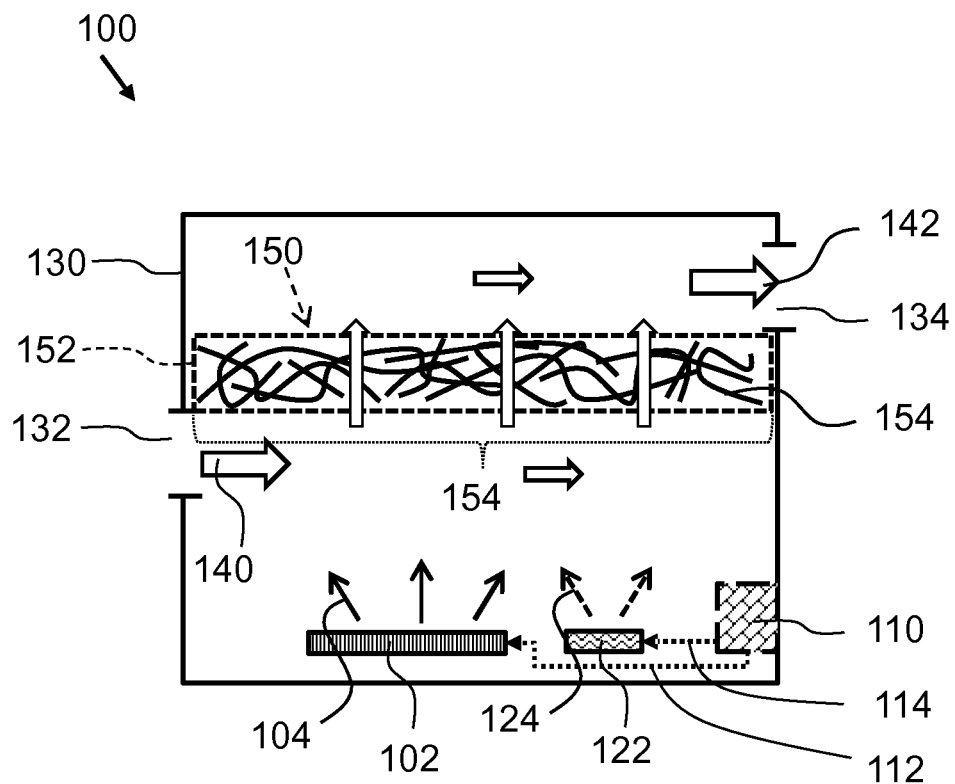
FIG. 1a schematically shows in a cross-sectional view an embodiment of an air purification device, FIG. 1b schematically shows embodiments of a light emission spectra of the first solid state light emitter and of the second solid state light emitter, FIG. 2 schematically shows in an exploded view of a portion of another embodiment air purification device, FIG. 3a schematically shows in an exploded view an embodiment of a photocatalytic volume, FIG. 3b schematically shows in a cross-sectional view another embodiment of a photocatalytic volume, FIG. 4a schematically shows a three dimensional view of a lighting device, FIGS. 4b and 4c schematically show possible embodiments of cross-sectional views the lighting device of FIG. 4a along line IV-IV', and FIG. 5 schematically shows an interior of a space of a building which comprise two different embodiments of a luminaire.

It should be noted that items denoted by the same reference numerals in different Figures have the same structural features and the same functions, or are the same signals. Where the function and/or structure of such an item have been explained, there is no necessity for repeated explanation thereof in the detailed description.

The Figures are purely diagrammatic and not drawn to scale. Particularly for clarity, some dimensions are exaggerated strongly.

DETAILED DESCRIPTION

FIG. 1a schematically shows in a cross-sectional view an embodiment of an air purification device 100. The air purification device 100 comprising a housing 130 that has an air inlet 132 for receiving an (input) air flow 140, an air outlet 134 for providing an (output) air flow 142 and an air purification volume 150 of which an envelope 152 is schematically shown by a dashed line.

The photocatalytic volume 150 is arranged in between the air inlet 132 and the air outlet 134. The photocatalytic volume 150 is arranged to allow air to flow through the photocatalytic volume 150. In the embodiment of FIG. 1a about the whole (input) air flow 140 shall go through the photocatalytic volume 150. This means that the photocatalytic volume 150 has at least air passages (not explicitly shown) through which the air can flow. The photocatalytic volume 150 comprises photocatalytic material that is provided at at least a portion of surfaces of the photocatalytic volume 150 along which, in use, the air flows. Thus, in practical embodiments, at least a portion of the surfaces that face the air passages comprises photocatalytic material. The photocatalytic material is configured to be a catalyst under the influence of UV light in photoreactions between gasses in the air that flow, in use, through the photocatalytic volume 150. In the specific embodiment of FIG. 1a, the photocatalytic volume comprises fibers 154 that form together, in a non-woven configuration, the photocatalytic volume 150. Between the fibers 154 are still open spaces present that allow the air the flow through the photocatalytic volume 150. Portions of surfaces of the fibers 154 are coated with the photocatalytic material.

The air purification device 100 also comprises a first solid state light emitter 102 and a second solid state light emitter 122. The first solid state light emitter 102 is configured to emit UV (Ultra Violet) light 104. The light beam that is emitted by the first solid state light emitter and the location where the solid state light emitter 102 is arranged within the air purification device 100 are selected such that the UV light 104 is transmitted towards the photocatalytic volume 150 to allow the UV light 104 to activate the photocatalytic material of the photocatalytic volume 150. Thus, when the first solid state light emitter 102 is emitting UV light 104 and the air inlet 132 receives the (input) air flow 140, the air purification device 100 removes at least a portion of smelly or hazardous gasses from the air flow 140 and provides through the air outlet 134 an (output) air flow 142 that is cleaner than the (input) air flow 140. Embodiments of the air purification device 100 are not limited to embodiment with a single first solid state light emitter. In an embodiment, the air purification device comprises a plurality of solid state light emitter emitting UV light 104 to the photocatalytic volume. Such a plurality of solid state light emitters emitting UV light 104 may be arranged in a one or two dimensional array or may be arranged in a specific 3d configuration to obtain the best illumination of the photocatalytic volume 150.

The second solid state light emitter 122 emits deep blue light 124 towards the photocatalytic volume 150 for disinfecting the photocatalytic volume 150. The deep blue light 124 has a specific light emission spectrum that has its peak wavelength in a range from 400 nanometer to 450 nanometer. The deep blue light 124 with wavelengths in this range effective kill and/or inactivate bacteria and thereby prevents that colonies of bacteria may grow in the photocatalytic volume 150. In another embodiment, the peak wavelength is in a range from 405 nanometer to 445 nanometer. In a further embodiment, the peak wavelength is in a range from 415 to 435 nanometer. The deep blue light 124 impinges on the photocatalytic volume 150 at a portion of a specific surface or side of the photocatalytic volume 150. This surface or side is not always (e.g. because of the non-woven structure of the fibess 154) a well-defined, surface, but we assume in this document that when a virtual envelope 152 is drawn around the photocatalytic volume 150, the virtual envelope 152 defines (virtual) surfaces 154 of the photocatalytic volume 150. Thus, the deep blue light 124 impinges on a portion of the (virtual) surfaces 154 of the photocatalytic volume 150 and, in an embodiment, the light energy density of the deep blue light 124 that impinges on this portion is in a range from 10 to 30 milli Watt hour per square centimeter (mWh/cm$^2$). This light energy density is determined at the (virtual) surface(s) of the photocatalytic volume 150 where the deep blue light 124 impinges on the photocatalytic volume 150. Optionally, the light energy density of the deep blue light 124, as measured at the (virtual) surfaces surface(s) of the photocatalytic volume 150, is in a range from 15 to 25 mWh/cm$^2$. The light energy density of the deep blue light 124 at the (virtual) surface(s) 154 of the photocatalytic volume 150 depend on the amount of light emitted by the second solid state light emitter 122, the width of the light beam emitted by the second solid state light emitter 122, the distance between the photocatalytic volume 150 and the second solid state light emitter 122, and other optional optical effects occurring on a light transmission path of the deep blue light 124 (such as, for example, reflections of the deep blue light 124 by walls of the housing 130). In practical embodiments, the amount of power to be emitted by the solid state light emitter 122 may be relatively low, for example lower than 0.5 Watt. It is to be noted that, in an embodiment, the air purification device 100, comprises a plurality of second solid state light emitters 122 emitting deep blue light 124 towards the photocatalytic volume 150. Such a plurality of second solid state light emitters 122 may be arranged, e.g. together with a plurality of first solid state light emitters 102, in a one or two dimensional array or may be arranged in a specific 3d configuration that allows a good illumination of the photocatalytic volume 150.

Optionally, the air purification device 100 comprises a controller 110. The controller 110 is coupled to the first solid state light emitter 102 and/or the second solid state light emitter 122 and provides optional control signals 112, 114 to the respective solid state light emitters 102, 122 to control their on and off state. The controller 110 may control the air purification operation of the air purification device 100 by controlling, for example, the first solid state light emitter 102 in the on and off state. The air purification device 100 may also comprise an air flow generator, such as a fan or ventilator, and the controller 110 may be configured to control the operation of the air flow generator as well. The controller 110 may also be configured to control the second solid state light emitter 122 in the on or off state to obtain an effective disinfection of the photocatalytic volume 150. In an example, the controller 110 controls the second solid state light emitter 122 at regular intervals of time in the on state for a specific period of time to obtain sufficient disinfection of the photocatalytic volume 150. In an example, the controller 110 controls the second solid state light emitter 122 in the on state while the first solid state light emitter 122 is also controlled in the on state. In an advantageous additional example, the controller 110 controls the second solid state light emitter 122 also in the on state while the first solid state light emitter 122 is in the off state to continue the disinfection of the photocatalytic volume while the air purification device 100 does not actively purify the air flow 140. The control signals 112, 114 may be low-power signals to control a driving circuitry that drives the respective solid state light emitters 102, 122. The control signals 112, 114 may also be the driving signals of the solid state light emitters 102, 122 when the controller 110 is configured to generate such high power signals.

Figure 1B:
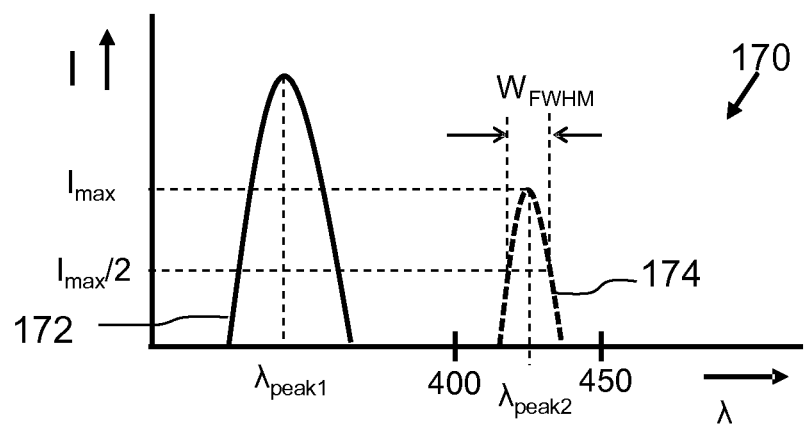

FIG. 1*b* schematically shows embodiments of a light emission spectra 172, 174 of the first solid state light emitter 102 and of the second solid state light emitter 122 respectively. The x-axis of chart 170 represents the wavelength λ of the emitted light, while the y-axis represents the (normalized) intensity I of the emitted light. Light emission spectrum 172 is an example of a light emission spectrum of the first solid state light emitter 102. The light emission spectrum 172 represents UV light, and, thus, its peak wavelength $\lambda_{peak1}$ is at least smaller than 400 nanometer. Optionally, about all wavelengths of the light emission spectrum 172 are below 400 nanometer. Optionally, the peak wavelength $\lambda_{peak1}$ of the light emission spectrum 172 is in a range from 300 nanometer and 400 nanometer. Optionally, about all wavelengths of the light emission spectrum 172 are in the range from 300 nanometer to 400 nanometer. Light emission spectrum 174 is an example of a light emission spectrum of the second solid state light emitter 122 and represents deep blue light. A peak wavelength $\lambda_{peak2}$ of the light emission spectrum 174 is in between 400 and 450 nanometer, optionally, in between 405 and 445 nanometer, and optionally, in between 415 and 435 nanometer. In an embodiment, a width $W_{FWHM}$ of the light emission spectrum 174, when reassured as a Full Width Half Maximum value, is smaller than 75 nanometer, optionally smaller than 50 nanometer, or optionally smaller than 35 nanometer.

Optionally, the deep blue light 124 emitted by the second solid state light emitter 122 does not only impinge on the photocatalytic volume 150, but impinges also on other components of the air purification device 100. For example, the deep blue light 122 light may impinge on portions of the (inner) walls of the housing 130 to disinfect the walls and to prevent the growing of bacteria colonies on the walls. The air inlet 132 may comprise, for example, an air inlet filter and the deep blue light 122 may also impinge on the air inlet filter to prevent that bacteria start to grow in the air passages of that air inlet filter. Optionally, the photocatalytic volume 150 is partially light transmitting for the deep blue light 122. This means that a portion of the deep blue light 122 that impinges on the (virtual) surface 154 of the photocatalytic volume 150 leaves the photocatalytic volume 150 at another surface, for example, an opposite surface. When the deep blue light 122 is partially transmitted through the photocatalytic volume 150, the air passages inside the photocatalytic volume 150 are also well disinfected and components at another side of the photocatalytic volume 150 may also be disinfected.

Skilled persons in the field of air purification know suitable photocatalytic materials which assist in reactions between gasses in the air flow under the influence of UV light. These materials are a catalyst which accelerate a photoreaction. In the context of air purification and, thus, in the context of this invention, they assist, under influence of light of a specific wavelengths, in reactions between gasses in the air flow such that hazardous or unpleasant gasses in the air flow are eliminated. The photocatalytic materials only operate as a good catalyst when they receive light of the specific wavelengths. In the context of the invention these specific wavelengths are in the UV spectral range. Well known examples of photocatalytic materials which may be used to purify air are: $TiO_2$, $SrTiO_3$, $Na_2Ti_6O_{13}$, $BaTi_4O_3$, $K_2La_2Ti_3O_{10}$, $ZrO_2$, $K_4Nb_6O_{17}$, $Sr_2Nb_2O_7$, $K_3Ta_3Si_2O_{13}$, $LiTaO_3$, $NaTaO_3$, $KTaO_3$, $BaTa_2O_6$, $CaTa_2O_6$, $RbNdTa_2O_7$, $SrTa_2O_6$, $Sr_2Ta_2O_7$, $RbNbWO_6$, $RbTaWO_6$, $CsNbWO_6$, $CsTaWO_6$, $ZnGa_2O_4$, $LiInO_2$, $NaInO_2$, $CaIn_2O_4$, $SrIn_2O_4$, $Zn_2GeO_4$, $Sr_2SnO_4$, $NaSbO_3$, $CaSb_2O_6$, $Ca_2Sb_2O_7$, $Sr_2Sb_2O_7$, $LaTiO_2N$, $CaNbO_2N$, $TaON$, $Ta_3N_5$, $CaTaO_2N$, $SrTaO_2N$, $BaTaO_2N$, $LaTaO_2N$, $TiON_x$, $Ti_{1-x}Ta_xO_{2-x}N_x$, $LaTaON_2$, $TiO_{2-2x}N_xF_x$, $TiO_2$ doped with transition metal ions to induce absorption in the visible part of the spectrum, such as Fe or Co, $TiO_2$ in a quasi two dimensional structure with a reduced bandgap (see, for example, Nature Chemistry, Volume 3, Issue 4, pp. 296-300 (2011)). Alternatively, materials can be used that generate reactive $^1O_2$ on irradiation with light, the reactive $^1O_2$ in turn does the actual purification reaction. Such materials comprise, for example: Indocyanine green, Phthalocyanine, Methylene blue, Sulforhodamine 101, Bengal rose, Tetraphenylporphyrine, Bacteriachlorophyll a, Coumarin 6, Coumarin 343, Coumarin 314, Coumarin 30, DCV-5T.

$TiO_2$ is an advantageous photocatalytic material when it receives Ultra Violet (UV) light. $TiO_2$ may also comprises C or N in its crystal structure such that $TiO_{(2-x)}:C_x$ is obtained or $TiO_{(2-y)}:N_y$. These from pure $TiO_2$ derived materials are also sensitive for UV light.

Examples of solid state light emitters are Light Emitting Diodes (LEDs), Organic Light Emitting diode(s) OLEDs, or, for example, laser diodes.

Figure 2:
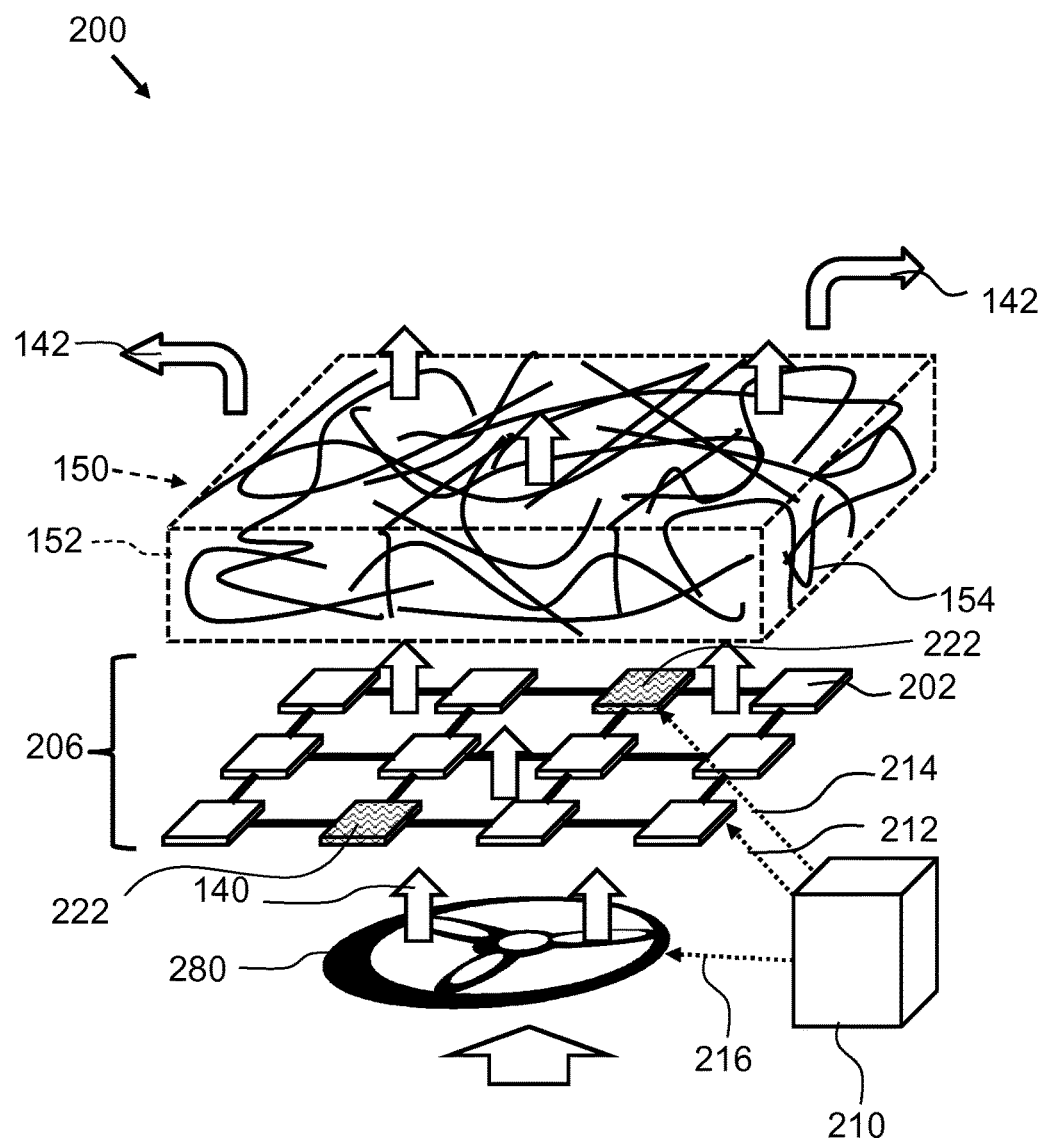

FIG. 2 schematically shows in an exploded view another embodiment of a portion of an air purification device 200. In FIG. 2 a housing of the air purification device 200 is not shown, but the housing comprises the elements show in FIG. 2 and comprises an air inlet and an air outlet. The embodiment of FIG. 2 shows the photocatalytic volume 150 that is about equal to the photocatalytic volume 150 of FIG. 1. The air purification device 200 has, instead of one first solid state light emitter and a second solid state light emitter, a two dimensional array 206 of solid state light emitters 202, 222.

The two dimensional array 206 has a plurality of first solid state light emitters 202 (non-dashed) and two second solid state light emitters 222 (dashed). The first solid state light emitters 202 are configured to emit UV light towards the photocatalytic volume 150 and the second solid state light emitters 222 are configured to emit deep blue light towards the photocatalytic volume 150. Embodiments of the UV light and the deep blue light are discussed in the context of FIG. 1a and FIG. 1b. The solid state light emitters 202, 222 of the array 206 are coupled to each other by power lines. Optionally, the array 206 also comprises driving circuitries and/or electrical connections that transmit control signals 212, 214 indicating whether the first solid state light emitters 202 and/or the second solid state light emitters 222 have to emit light. Such control signal 212, 214 may be generated by a controller 210 which generated such signals in accordance to the embodiments discussed in the context of FIG. 1a. The embodiment of the air purification unit 200 also comprises a ventilator 280 which generates, in use, an (input) air flow 140 which is transferred towards the photocatalytic volume 150. The array 206 of solid state light emitters 202, 222 may be arranged in between the ventilator 280 and the photocatalytic volume 150 such that the solid state light emitter 202, 222 are cooled by the generated air flow 140. The ventilator 280 is arranged to suck air from outside the housing of the air purification device through the air inlet. Optionally, the controller 210 is also configured to generate a control signal 216 for controlling the on and off state the ventilator 280. The control signal 216 may be provided to a driving circuitry of the ventilator 280, or the controller 210 may be configured to generate a power signal for directly driving the ventilator 280. The controller, for example, controls the plurality of first solid state light emitters 202 and the ventilator 280 at the same moment in time in the on-state.

It is to be noted that embodiments of the air purification device 200 does not necessary include the ventilator 280 or another means for generating the (input) air flow 140. In other embodiments, the air inlet of the air purification device is coupled to, for example, an air outlet of an air refreshment or air conditioning system of a building for receiving the air flow. In a further embodiments, the air outlet of the air purification device may be coupled to an air inlet of the air refreshment or air conditioning system such thereby an air flow through the air purification device is obtained, and, thus, the air inlet receives an air flow.

Figure 3A:
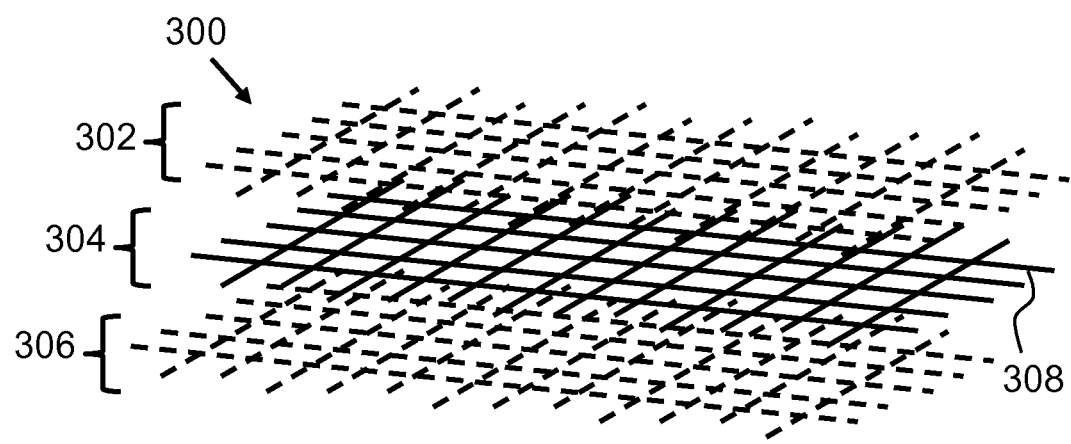
Figure 3B:
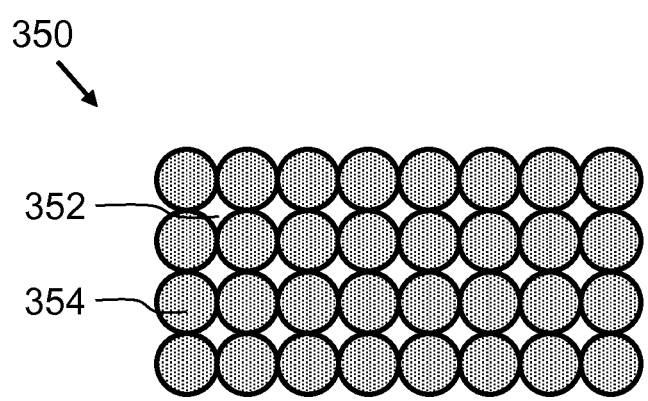

FIG. 3a schematically shows in an exploded view an embodiment of a photocatalytic volume 300. FIG. 3b schematically shows in a cross-sectional view another embodiment of a photocatalytic volume 350. The photocatalytic volumes 300, 350 comprise elongated structures on which, on at least a portion of their surfaces, the photocatalytic material is provided.

In FIG. 3a a three dimensional view is provided of a photocatalytic volume 300 which is formed by a structure of three layers 302, 304, 306 of woven wires or fibers 308, such as glass or quarts fibers or aluminum oxide or aluminum nano-wires. Photocatalytic material is provided on the wires or fibers 308. In FIG. 3a the three layers 302, 304, 306 are not drawn directly on top of each other, but in practical embodiments, layers of woven elongated elements are laid on top of each other.

FIG. 3b presents a cross-sectional view of another embodiment of a photocatalytic volume 350. The photocatalytic volume 350 comprises several thin rods 354 which are brought in contact with each other in an array-like structure. The rods 354 are, for example, glued or soldered to each other in an axial direction. In between the rods 354 are open spaces 352 which extends in the axial direction (of the rods 354) from one side of the photocatalytic volume 350 to an opposite side of the photocatalytic volume 350. Surfaces of the rods 354 which face the open spaces 352 are coated with a layer of a photocatalytic material.

In alternative embodiments of the photocatalytic volume 350, the shaded circles 354 of FIG. 3b form hollow channels from one side of the photocatalytic volume 350 to an opposite side of the photocatalytic volume 350 and the surfaces facing the hollow channels are coated with the photocatalytic material. The "white" areas indicated with 352 may be a solid material. Thus, the photocatalytic material 350 may be formed by bars 352 and open spaces 354 in between the bars 352.

In an alternative embodiment of the photocatalytic volume 350, the drawn shaded circles 354 are cross-sectional views of thin tubes which touch each other in the axial direction. As well as the tubes as the spaces 352 in between the tubes form a passage for air and all surfaces of the tubes may be coated with a photocatalytic material.

Figure 4A:
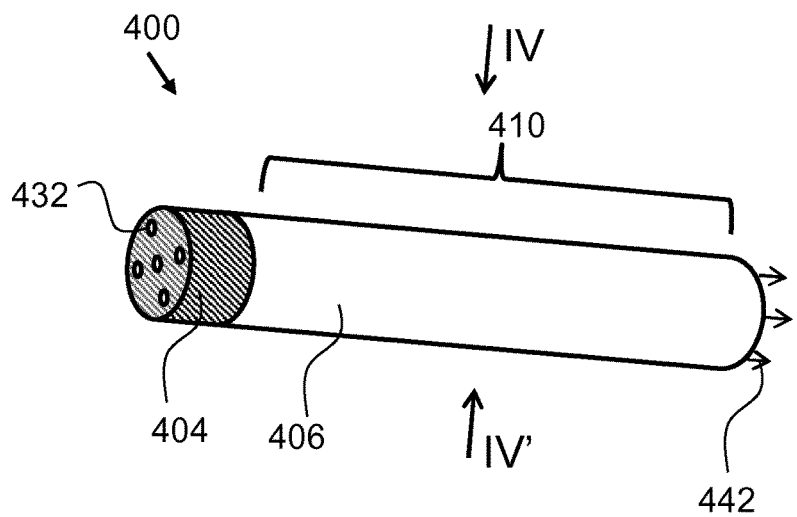

FIG. 4a schematically shows a three dimensional view of a lighting device 400. The lighting device 400 comprises a light tube 406 which is at least partly transparent such that a light exit window 410 is obtained. At a first end of the light tube an air flow creation unit 404 is provided which comprises holes 432 through which air is drawn into the light tube 406. At a second end of the light tube, which is opposite the first end, the purified air 442 leaves the air tube through holes. Thus, the air inlet is formed by the holes 432 and the air flow creation unit 404, and the air outlet is formed by holes (not shown) at the second end. The light tube 406 may be made of, for example, glass or of a synthetic material. At least a portion of the light tube 406 is light transmitting and has the function of light exit window 410. The light exit window 410 may be transparent or translucent and, at least, is capable of transmitting light that is visible to the human naked eye.

Figure 4B:
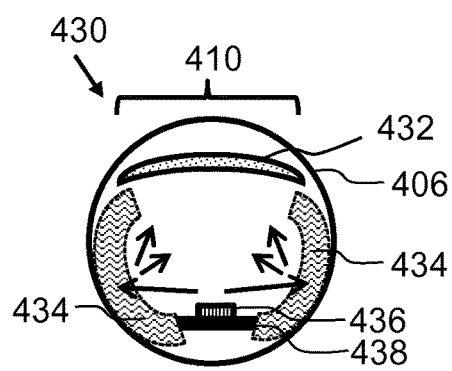
Figure 4C:
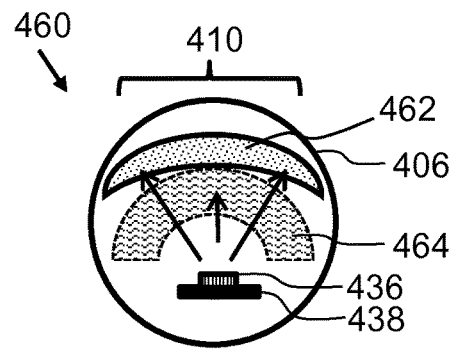

FIGS. 4b and 4c schematically show possible embodiments of cross-sectional views the lighting device of FIG. 4a along line IV-IV', and FIG. 4b presents a first embodiment with a photocatalytic volume 434 in a light reflective arrangement and FIG. 4c presents a second embodiment with a photocatalytic volume 464 in a light transmissive arrangement.

The cross-sectional view 430 of FIG. 4b shows that, within the light tube 406, a TLED strip 438/436, two photocatalytic volumes 434 and a luminescent element 432 are provided. All the elements within the light tube 406 have an elongated shape and extend within the light tube 406 in an axial direction. The TLED strip 438/436 comprises an elongated supporting strip 438 (which may be a printed circuit board) on which a plurality of LEDs 436 are provided which emit light in a direction away from the TLED strip 438/436. Two types of LEDs are provided on the TLED strip 438/436: LEDs that emit UV light and LEDs that emit deep blue light. Embodiments of the UV light and the deep blue light have been discussed previously in the context of for example FIG. 1a. The LEDs 436 may have a Lambertian angular light emission distribution and, therefore, some light is also emitted in a sideward direction towards the photocatalytic volumes 434. The photocatalytic volumes 434 are, for example, made of fibers which comprise at their surface a photocatalytic material. The photocatalytic volumes 434 are configured such that they, at least, partially reflect light which impinges on the fibers which photocatalytic material. For example, when the density of fibers in the photocatalytic volume 434 is relatively large and, for example, $TiO_2$ is provided as a photocatalytic material, the $TiO_2$ reflects and scatters light and, consequently, a portion of the light which is reflected back into the light tube is also emitted towards the luminescent element 432. The luminescent element 432 at least comprises a layer of luminescent material which converts UV light towards visible light. The light emission of the lighting device 400 comprise the visible light. Preferably the light tube 406 filters the light that is emitted into the ambient such that the UV light is not transmitted into the ambient.

The cross-sectional view 460 of FIG. 4c represents a lighting unit which is similar to the lighting unit 430 of FIG. 4b and which has also the discussed elements of the lighting device 400 of FIG. 4a. However, the lighting device of FIG. 4c comprises another luminescent element 462 and another photocatalytic volume 464. The photocatalytic volume 464 is arranged in between the TLED strip 438/436 and the luminescent element 462. The photocatalytic volume 464 may be a woven or non-woven elongated elements made of very thin wires or made of fibers which comprises a photocatalytic material at their surfaces. The density of the photocatalytic volume 464 is chosen such that light which enters the photocatalytic volume 464 at a first side is (at least partly) transmitted through the photocatalytic volume 464 to a second side of the photocatalytic volume 464. The transmission through the photocatalytic volume 464 may also include the reflection and scattering of the light. Thus, light which impinges on the luminescent element 462 is at least partly transmitted through the photocatalytic volume 464. The luminescent element 462 comprises at least a layer of luminescent material which converts UV towards visible light.

The embodiments of the lighting device 400 of FIGS. 4a, 4b, 4c may be configured to be used in a traditional luminaire which is suitable for traditional discharge tubes. Thus, the lighting device 400 may have at both ends two pins to connect to the mains power and the lighting device 400 may comprise an additional electric circuit to convert the power which is received via those two pins towards power which is suitable to use with the LEDs 436.

The skilled person in the field of lighting knows luminescent materials that are suitable for converting UV light towards visible light. For example, such luminescent materials are extensively used in fluorescent light tubes. Embodiments of the suitable luminescent materials may be, but are not limited to, organic phosphors, inorganic phosphors, quantum dots, quantum rods.

Figure 5:
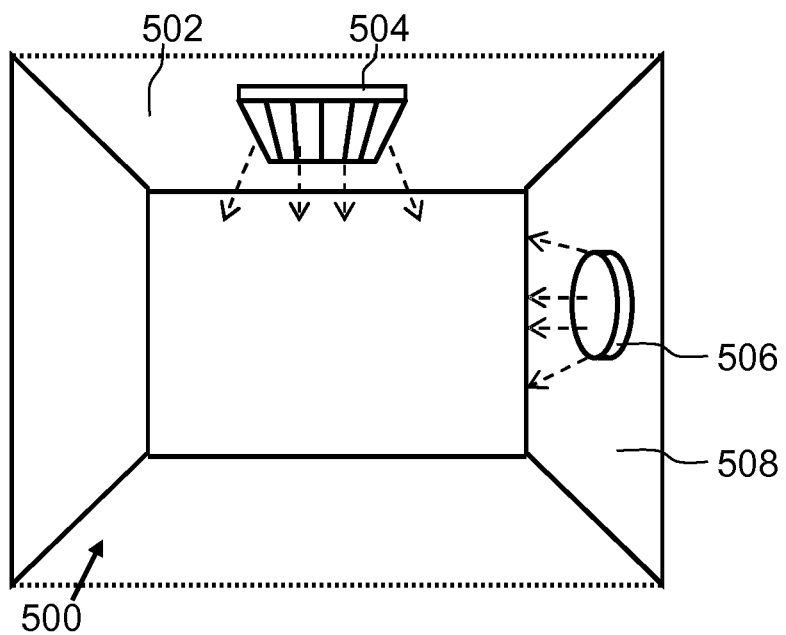

FIG. 5 schematically shows an interior of a room 500 comprising two luminaires 504, 506. At a ceiling 502 of the room 500 a luminaire 504 is provided which comprises lighting devices according to an aspect of the invention. For example, lighting devices 400 according to the embodiments of FIG. 4a, 4b or 4c are provided in the luminaire 504. At a wall 508 of the room 500 is provided a wall-luminaire which comprises a lighting device according to an aspect of the invention. The luminaires 504, 506 provide, beside illumination of the room 500, also the advantageous effect of air purification.

In summary, this document provides an air purification device, a lighting device and a luminaire are provided. The air purification device comprises an air inlet, an air outlet, a photocatalytic volume, a first solid state light emitter and a second solid state light emitter. The air inlet receives an air flow. The photocatalytic volume comprises a photocatalytic material and the air flow flows through the photocatalytic volume to contact some air with the photocatalytic material. The photocatalytic volume is between the air inlet and the air outlet. The photocatalytic material is a catalyst under the influence of UV light in photoreactions between gasses in the air flow. The first solid state light emitter emits UV light towards the photocatalytic volume. The second solid state light emitter emits deep blue light towards the photocatalytic volume. The deep blue light has a peak wavelength in between 400 nanometer and 450 nanometer.

Examples of an air purification device, a lighting device and a luminaire are defined in the following numbered clauses:

1. An air purification device (100, 200) for purifying air, the air purification device (100, 200) comprising
    an air inlet (132) for receiving an air flow (140),
    an air outlet (134),
    a photocatalytic volume (150, 300, 350, 434, 464) comprising a photocatalytic material, the photocatalytic volume (150, 300, 350, 434, 464) being arranged to allow air to flow through the photocatalytic volume (150, 300, 350, 434, 464) such that at least a portion of air flowing through the photocatalytic volume (150, 300, 350, 434, 464) contacts the photocatalytic material, the photocatalytic volume (150, 300, 350, 434, 464) being arranged between the air inlet (132) and the air outlet (134) to ensure that, in use, at least a portion of the air flow (140) received by the air inlet (132) flows through the photocatalytic volume (150, 300, 350, 434, 464), the photocatalytic material being configured to be a catalyst under the influence of UV light (104) in photoreactions between gasses in the air flowing through the photocatalytic volume (150, 300, 350, 434, 464),
    a first solid state light emitter (102, 202) arranged to emit UV light (104) and to emit the UV light (104) towards the photocatalytic volume (150, 300, 350, 434, 464) for activating the photocatalytic material to act as the catalyst,
    a second solid state light emitter (122, 222) arranged to emit deep blue light (124) in a light emission spectrum (174) having peak wavelength (λpeak2) in the range from 400 nanometer to 450 nanometer, the second solid state light emitter (122, 222) being arranged to emit the deep blue light (124) towards the photocatalytic volume.
2. An air purification device (100, 200) according to clause 1, wherein the light intensity of the second solid state light emitter (122, 222) is selected to obtain a light energy density of the deep blue light (124) in a range from 10 to 30 mWh/cm$^2$ at the photocatalytic volume (150, 300, 350, 434, 464).
3. An air purification device (100, 200) according to any one of the preceding clauses, wherein the peak wavelength (λpeak2) of the light emission spectrum of the deep blue light (124) is in a range from 415 to 435 nanometer.
4. An air purification device (100, 200) according to any one of the preceding clauses further comprising a controller (110) for controlling an on and off state of the second solid state light emitter (122, 222).
5. An air purification device (100, 200) according to clause 4, wherein the controller (110) is configured to control the second solid state light emitter (122, 222) also into the on state while the first solid state light emitter (102, 202) is not emitting light.
6. An air purification device (100, 200) according to any one of the preceding clauses, wherein the UV light (104) emitted by the first solid state light emitter (102, 202) has a peak wavelength in a range from 300 nanometer to 400 nanometer.
7. An air purification device (100, 200) according to any one of the preceding clauses, wherein the photocatalytic volume (150, 300, 350, 434, 464) comprises elongated structures (154, 308, 354) and the photocatalytic material being provided on at least a portion of the surfaces of the elongated structures (154, 308, 354).
8. An air purification device (100, 200) according to clause 7, wherein the elongated structures (154, 308, 354) are fibers (154, 308) and, optionally, the photocatalytic volume is a woven or non-woven material made of the fibers (154, 308).
9. An air purification device (100, 200) according to any one of the preceding clauses further comprising an air flow generator (280) for generating the air flow (140) received by the air inlet (132).
10. An air purification device (100, 200) according to any one of the preceding clauses, wherein the second solid state light emitter (122, 222) is arranged for emitting the deep blue light (124) towards other components of the air purification device (100, 200), such as for example towards a portion of an inner surface of a housing (130) of the air purification device (100, 200).
11. A lighting device (400, 430, 460) comprising a light source (436) and the air purification device (100, 200) according to any one of the preceding clauses.
12. A lighting device (400, 430, 460) according to clause 11, further comprising luminescent material (432, 462) being configured to convert UV light (104) towards visible light, wherein the luminescent material (432, 462) is arranged to receive a portion of UV light (104) emitted by the first solid state light emitter (102, 202) of the air purification device (100, 200), the lighting device (400, 430, 460) further comprising a light exit window (410) for emitting at least a portion of the visible light towards an ambient of the lighting device (400, 430, 460).
13. A luminaire (504, 506) comprising the lighting device (400, 430, 460) according to clause 11.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and the controller may be implements by means of a suitably programmed computer or processor. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An air purification device for purifying air, the air purification device comprising:
    an air inlet for receiving an air flow,
    an air outlet,
    a photocatalytic volume comprising a photocatalytic material, the photocatalytic volume being arranged to allow air to flow through the photocatalytic volume such that at least a portion of air flowing through the photocatalytic volume contacts the photocatalytic material, the photocatalytic volume being arranged between the air inlet and the air outlet to ensure that, in use, at least a portion of the air flow received by the air inlet flows through the photocatalytic volume, the photocatalytic material being configured to be a catalyst under the influence of UV light in photoreactions between gasses in the air flowing through the photocatalytic volume, a first solid state light emitter arranged to emit UV light and to emit the UV light towards the photocatalytic volume for activating the photocatalytic material to act as the catalyst, a second solid state light emitter arranged to emit deep blue light in a light emission spectrum having peak wavelength in the range from 400 nanometer to 450 nanometer, the second solid state light emitter being arranged to emit the deep blue light towards the photocatalytic volume, a controller for controlling an on and off state of the second solid state light emitter, wherein the controller is configured to control the second solid state light emitter also into the on state for at least a period of time while the first solid state light emitter is not emitting light.

2. An air purification device according to claim 1, wherein at least the period of time comprises one of: about the whole period of time that the first solid state light emitter is not emitting light, a limited period of time of the period of time that the first solid state light emitter is not emitting light, periods of time at regular or irregular intervals of time during the period of time that the first solid state light emitter is not emitting light.

3. An air purification device according to claim 1, wherein the light intensity of the second solid state light emitter is selected to obtain a light energy density of the deep blue light in a range from 10 to 30 mWh/cm² at the photocatalytic volume.

4. An air purification device according to claim 1, wherein the peak wavelength of the light emission spectrum of the deep blue light is in a range from 415 to 435 nanometer.

5. An air purification device according to claim 1, wherein the UV light emitted by the first solid state light emitter has a peak wavelength in a range from 300 nanometer to 400 nanometer.

6. An air purification device according to claim 1, wherein the photocatalytic volume comprises elongated structures and the photocatalytic material being provided on at least a portion of the surfaces of the elongated structures.

7. An air purification device according to claim 6, wherein the elongated structures are fibers and, optionally, the photocatalytic volume is a woven or non-woven material made of the fibers.

8. An air purification device according to claim 1, further comprising an air flow generator for generating the air flow received by the air inlet.

9. An air purification device according to claim 1, wherein the second solid state light emitter is arranged for emitting the deep blue light towards other components of the air purification device, such as for example towards a portion of an inner surface of a housing of the air purification device.

10. A lighting device comprising a light source and the air purification device according to claim 1.

11. A lighting device according to claim 10, further comprising luminescent material being configured to convert UV light towards visible light, wherein the luminescent material is arranged to receive a portion of UV light emitted by the first solid state light emitter of the air purification device, the lighting device further comprising a light exit window for emitting at least a portion of the visible light towards an ambient of the lighting device.

12. A luminaire comprising the lighting device according to claim 10.

* * * * *